US012773226B2

(12) United States Patent
Nishio

(10) Patent No.: US 12,773,226 B2
(45) Date of Patent: Oct. 27, 2026

(54) MEDICAL DEVICE

(71) Applicant: TERUMO KABUSHIKI KAISHA, Tokyo (JP)

(72) Inventor: Kosuke Nishio, Irvine, CA (US)

(73) Assignee: TERUMO KABUSHIKI KAISHA, Tokyo (JP)

(*) Notice: Subject to any disclaimer, the term of this patent is extended or adjusted under 35 U.S.C. 154(b) by 26 days.

(21) Appl. No.: 18/899,082

(22) Filed: Sep. 27, 2024

(65) Prior Publication Data

US 2025/0107816 A1 Apr. 3, 2025

(30) Foreign Application Priority Data

Sep. 29, 2023 (JP) ................................ 2023-169510

(51) Int. Cl.
*A61B 17/22* (2006.01)
*A61B 17/00* (2006.01)
*A61B 17/32* (2006.01)

(52) U.S. Cl.
CPC .............. *A61B 17/22* (2013.01); *A61B 17/32* (2013.01); *A61B 2017/00526* (2013.01); *A61B 2017/00831* (2013.01)

(58) Field of Classification Search
CPC ...... A61M 25/0045; A61M 2025/0046; A61M 25/0054; A61M 2025/006; A61B 17/22; A61B 17/32; A61B 2017/00526; A61B 2017/00831; A61B 2017/00309; A61B 2017/00858; A61B 2017/320004; A61B 17/320758
See application file for complete search history.

(56) References Cited

U.S. PATENT DOCUMENTS 8,628,549 B2 1/2014 To et al.

FOREIGN PATENT DOCUMENTS

| | | | | |
|---|---|---|---|---|
| EP | 3067087 A1 * | 9/2016 | ........ | A61M 25/1006 |
| EP | 3569264 A1 * | 11/2019 | ............. | H01B 11/20 |
| WO | WO-2010018762 A1 * | 2/2010 | ............ | A61M 25/09 |

* cited by examiner

*Primary Examiner* — Ashley L Fishback
(74) *Attorney, Agent, or Firm* — BUCHANAN INGERSOLL & ROONEY PC

(57) ABSTRACT

A medical device including a long shaft, the shaft including a distal end tube made of metal, the distal end tube provided with a distal end side rough surface portion having an uneven shape provided on an outer surface of a distal end, a proximal end side rough surface portion having an uneven shape provided on an outer surface of a proximal end, and an intermediate portion as a region between the distal end side rough surface portion and the proximal end side rough surface portion including a smooth outer surface, the distal end tube including an outer surface covered with a covering material made of resin, and the covering material being in close contact with the distal end side rough surface portion and the proximal end side rough surface portion.

20 Claims, 5 Drawing Sheets

FIG. 3
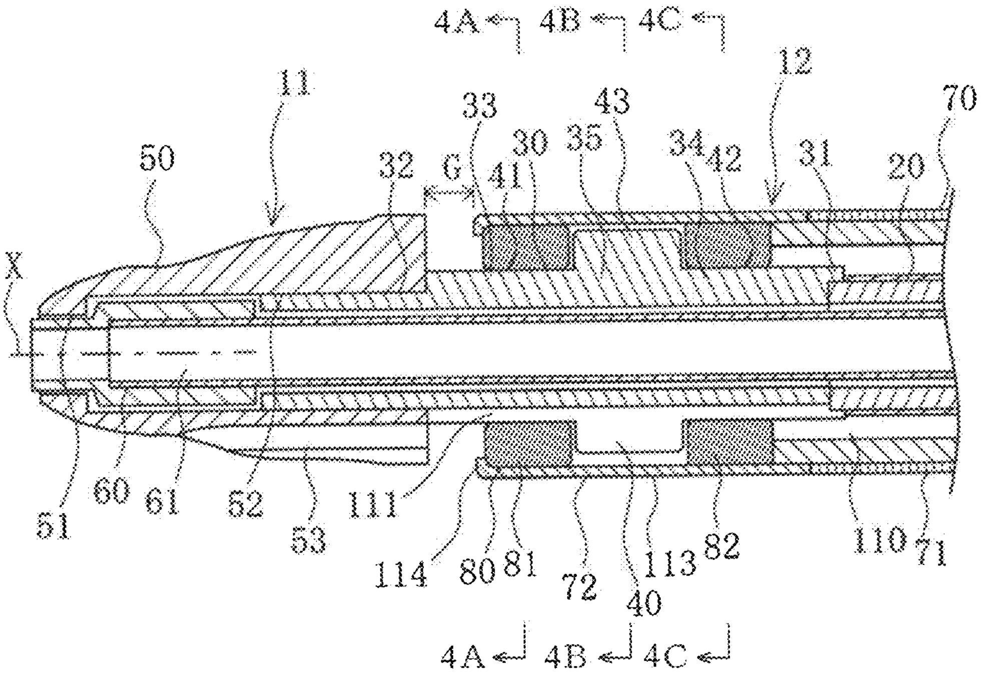
FIG. 4A
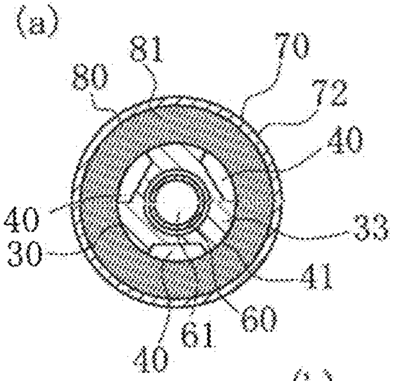
FIG. 4C
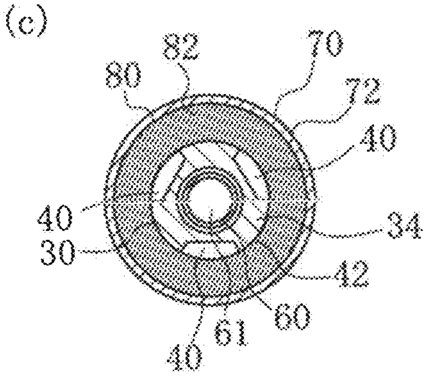
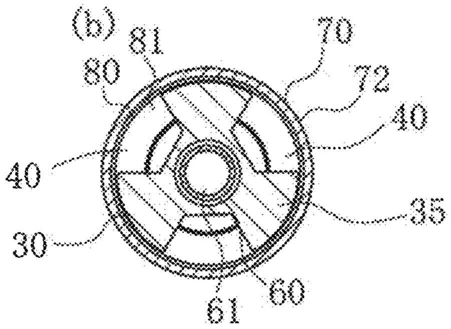
FIG. 4B

MEDICAL DEVICE

CROSS-REFERENCES TO RELATED APPLICATIONS

This application claims priority to Japanese Patent Application No. 2023-169510 filed on Sep. 29, 2023, the entire content of which is incorporated herein by reference.

TECHNOLOGICAL FIELD

The present invention generally relates to a medical device including a long shaft.

BACKGROUND DISCUSSION

As a method of treating a lesion such as stenosis or occlusion generated in a blood vessel, there is an endovascular treatment in which treatment is performed from inside the blood vessel using a device percutaneously inserted into the blood vessel. In endovascular treatment, a catheter is used for allowing a medical treatment device to reach a lesion.

For example, as the catheter for cutting and removing stenosis such as thrombus, plaque, or a calcified lesion in the blood vessel, a tube made of metal may be used as a long shaft. Since the blood vessel is bent, the shaft comes into sliding contact with a blood vessel wall when the shaft is inserted toward the lesion. When friction between the blood vessel wall and the shaft is large, torque is accumulated in the shaft as the shaft is advanced in the blood vessel.

For example, U.S. Pat. No. 8,628,549 discloses that, in a catheter including a tube made of metal, a covering material made of resin is provided on a surface of the tube made of metal. Since the covering material has a friction coefficient lower than that of metal, it is possible to control friction with the blood vessel wall to be low at the time of insertion into the blood vessel and to prevent accumulation of torque in the shaft.

SUMMARY

However, since the covering material made of resin is provided on a surface of a distal end of the tube and this comes in close contact with the surface of the tube made of metal, flexibility of an entire shaft decreases, and passability in the blood vessel decreases.

The medical device disclosed here is capable of decreasing friction with a blood vessel wall while preventing a decrease in flexibility of a shaft.

A medical device comprises an elongated shaft that includes a distal end tube made of metal, the distal end tube provided with a distal end side rough surface portion having an uneven shape provided on an outer surface of a distal end, a proximal end side rough surface portion having an uneven shape provided on an outer surface of a proximal end, and an intermediate portion as a region between the distal end side rough surface portion and the proximal end side rough surface portion including a smooth outer surface, the distal end tube including an outer surface covered with a covering material made of resin, and the covering material being in close contact with the distal end side rough surface portion and the proximal end side rough surface portion.

In the medical device configured as described above, since the covering material enters the uneven shape of the distal end tube on the distal end side rough surface portion and the proximal end side rough surface portion and is closely fixed, it is possible to increase fixing strength of the covering material with respect to the distal end tube for decreasing friction with the blood vessel wall. In the medical device, since the outer surface of the intermediate portion of the distal end tube is smooth, the covering material does not enter the uneven shape, and a decrease in flexibility can be prevented.

According to another aspect, a medical device positionable in a biological lumen comprises: a rotatable shaft; a cutter configured to cut an object located in the biological lumen, the cutter being connected to the shaft so that rotation of the shaft results in rotation of the cutter; and an outer tubular main body in which the rotatable shaft is positioned, with the outer tubular main body having a distal end and the cutter being positioned distal of the distal end of the outer tubular main body. The outer tubular main body includes a distal end metal tube constituting a distal portion of the outer tubular main body, and the distal end metal tube including a first rough surface portion having an uneven outer surface and a second rough surface portion having an uneven outer surface, with the first rough surface portion being located distal of the second rough surface portion. The uneven outer surface of the first rough surface portion extending from a distal end of the first rough surface portion to a proximal end of the first rough surface portion, and the uneven outer surface of the second rough surface portion extending from a distal end of the second rough surface portion to a proximal end of the second rough surface portion. The proximal end of the first rough surface portion is spaced apart from the distal end of the second rough surface portion, with an intermediate portion of the distal end metal tube being located between the proximal end of the first rough surface portion and the distal end of the second rough surface portion. The intermediate portion of the distal end metal tube has an outer surface configured differently from the uneven outer surface of the first rough surface portion and the uneven outer surface of the second rough surface portion. The distal end metal tube includes a covering material made of resin, the covering material made of resin covering: i) the uneven outer surface of the first rough surface portion of the distal end metal tube; ii) the intermediate portion of the distal end metal tube; and iii) the uneven outer surface of the second rough surface portion of the distal end metal tube.

Another aspect of the disclosure involves a method for producing a distal end tube forming part of a medical device that is positionable in a biological lumen. The method comprises: performing roughening processing on first and second portions of an outer surface of a metal tube that is configured to be positioned in the biological lumen, wherein the performing of the roughening processing includes: i) performing the roughening processing on the first portion of the outer surface of the metal tube to produce a first rough surface portion having an uneven outer surface; and ii) performing the roughening processing on the second portion of the outer surface of the metal tube to produce a second rough surface portion having an uneven outer surface. The performing of the roughening processing is carried out so that: i) the first rough surface portion is located distal of the second rough surface portion; ii) the uneven outer surface of the first rough surface portion extends from a distal end of the first rough surface portion to a proximal end of the first rough surface portion; iii) the uneven outer surface of the second rough surface portion extends from a distal end of the second rough surface portion to a proximal end of the second rough surface portion; and i) the proximal end of the first rough surface portion is spaced apart from the distal end of the second rough surface portion. The roughening processing is performed on the outer surface of the first portion of the metal tube and on the outer surface of the second portion of the metal tube so that the outer surface of an intermediate portion of the metal tube is a smooth outer surface, the intermediate portion of the metal tube having the smooth outer surface being located between the proximal end of the first rough surface portion and the distal end of the second rough surface portion. The method additionally involves fixing a covering material made of resin to the metal tube so that the covering material covers the uneven outer surface of the first rough surface portion of the metal tube, the uneven outer surface of the second rough surface portion of the metal tube and the smooth outer surface of the intermediate portion of the metal tube. The covering material made of resin is in contact with the uneven outer surface of the first rough surface portion and the uneven outer surface of the second rough surface portion.

BRIEF DESCRIPTION OF THE DRAWINGS

FIG. 3 is a cross-sectional view illustrating the distal end of the medical device.

FIGS. 4A to 4C illustrate the distal end of the medical device in which FIG. 4A is a cross-sectional view taken along the section 4A-4A in FIG. 3, FIG. 4B is a cross-sectional view taken along the section line 4B-4B in FIG. 3, and FIG. 4C is a cross-sectional view taken along the section line 4C-4C in FIG. 3.

DETAILED DESCRIPTION

Figure 1:
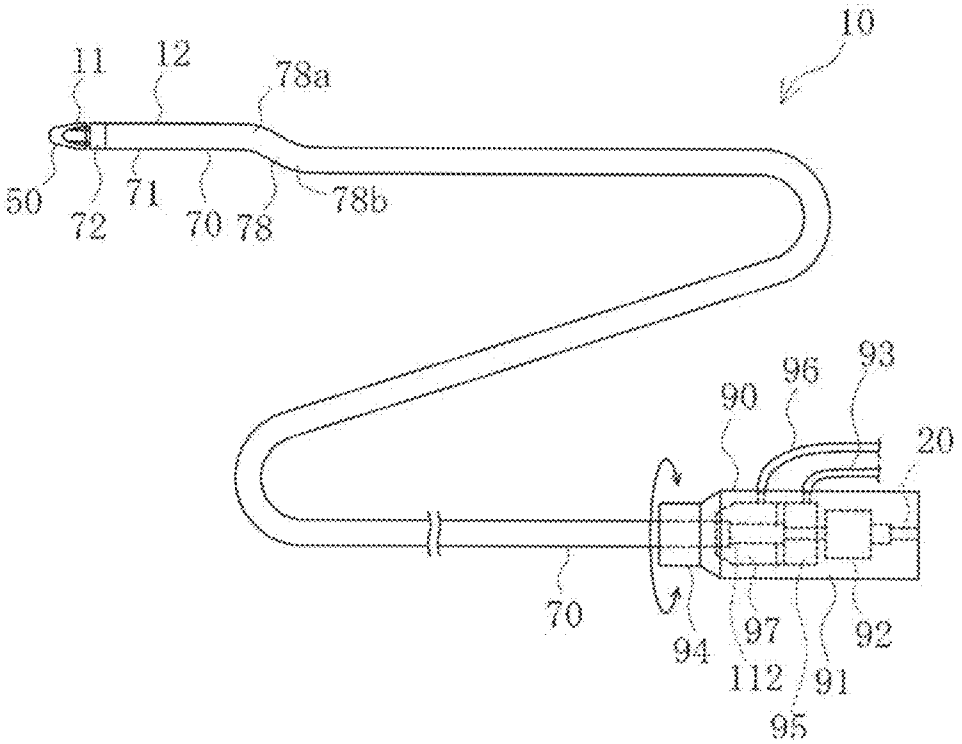
FIG. 1 is a front view illustrating a medical device according to an embodiment.

Hereinafter, an embodiment of the medical device disclosed here, representing one example of the new medical device, is described with reference to the drawings. The dimensions of the drawings may be exaggerated and different from actual dimensions for convenience of description in some cases. In the present specification and the drawings, components having substantially the same functional configuration are denoted by the same reference numeral, and a detailed description of such features may not be repeated. In the present specification, a side to be inserted into a lumen is referred to as a "distal end side", and a side to be operated is referred to as a "proximal end side".

A medical device 10 according to the embodiment is inserted into a blood vessel and used for treatment of cutting and removing plaque, a calcified lesion or the like in acute lower limb ischemia or deep vein thrombosis. An object to be cut is not especially limited, and may be, for example, atheroma, thrombus or the like. Furthermore, all objects that may be present in a biological lumen may correspond to the object to be cut by the medical device 10.

Figure 2:
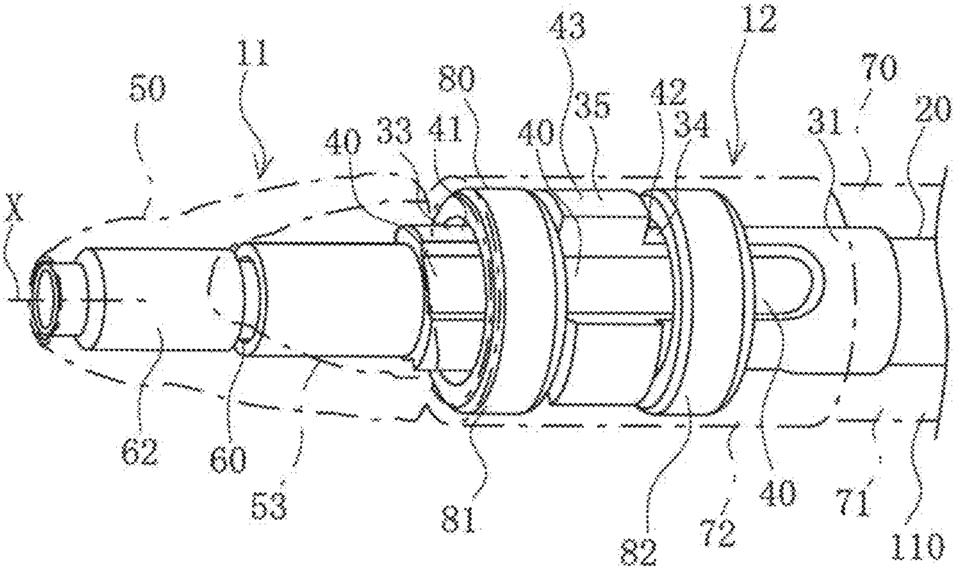
FIG. 2 is a perspective view illustrating a distal end of the medical device as seen through a cutter and a housing unit.

As illustrated in FIGS. 1 to 3, the medical device 10 is provided with a rotatable rotating structure 11, a housing unit 12 that rotatably houses the rotating structure 11, and a handle 90 operated by an operator. The rotating structure 11 is provided with a drive shaft 20 that transmits rotational force, a shaft portion 30 rotatably supported by the housing unit 12, a cutter 50 that cuts plaque and a calcified lesion, and a protection tube 60 housed in the drive shaft 20. The housing unit 12 is provided with an outer tubular shaft 70 that houses the drive shaft 20 and a bearing 80 that rotatably supports the shaft portion 30.

Figure 5:
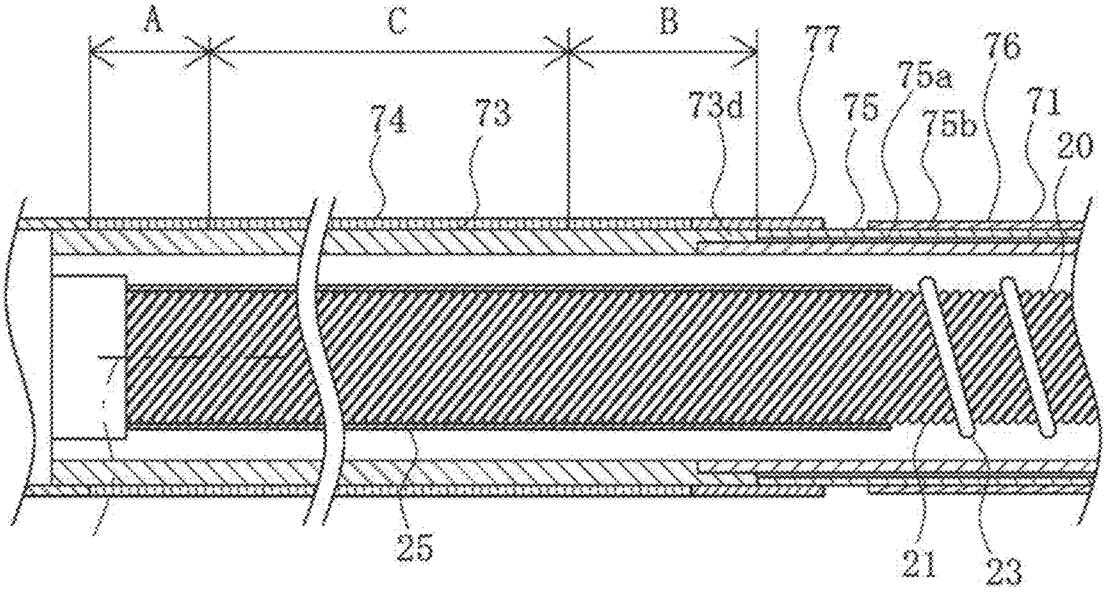
FIG. 5 is a cross-sectional view illustrating a portion on a proximal end side from FIG. 3 of the medical device, a front view of a drive shaft.

The drive shaft 20 is a long tube body (elongated tubular body). The drive shaft 20 is flexible and has a property capable of transmitting the rotational force applied from a proximal end side to a distal end side. The shaft portion 30 is fixed to a distal end of the drive shaft 20. As illustrated in FIG. 5, the drive shaft 20 is a tubular body in which a plurality of wire rods 21 is arranged and spirally coupled around an axis X of the rotating structure 11. The drive shaft 20 includes an additional coil 23 spirally wound around an outer peripheral surface thereof from a position on the proximal end side from the distal end toward the proximal end side. The additional coil 23 can generate a flow of fluid that conveys an object toward the proximal end side as the drive shaft 20 rotates. The axis X is a structural central axis of the rotating structure 11, the central axis of the rotating structure 11. A proximal end of the drive shaft 20 is located inside the handle 90. The drive shaft 20 is not necessarily formed of a wire rod.

A constituent material from which the drive shaft 20 may be fabricated is not especially limited as long as the material is metal, and for example, stainless steel, nitinol or the like can be suitably used.

The cutter 50 is a member for cutting the object such as the plaque and calcified lesion into small pieces as illustrated in FIGS. 1 to 3. Therefore, the term "cutting" is intended to mean an action of applying force to an object in contact with the same and making the object smaller (reducing the size of the object). An applying method of force during cutting and a shape or a mode of the cut object are not limited.

The cutter 50 includes a large number of fine abrasive grains on a surface thereof. The cutter 50 may also be provided with a sharp blade. In the cutter 50, a first through-hole 51 located on the distal end side and a second through-hole 52 located on the proximal end side from the first through-hole 51 are formed. The first through-hole 51 and the second through-hole 52 communicate with each other and penetrate the cutter 50 in a direction along the axis X. A distal end of the shaft portion 30 is fitted in the second through-hole 52 to be coupled.

An outer peripheral surface of the cutter 50 includes a groove-shaped cutout 53 extending in the direction along the axis X. The cutout 53 functions as a flow path for conveying the cut object in a proximal end direction. The cutouts 53 are arranged, for example, at intervals of 120 degrees in a circumferential direction. Therefore, the cutter 50 includes three cutouts 53 regularly arranged in the circumferential direction. An edge of each cutout 53 is smoothly formed with a curvature. The number of the cutouts 53 is not limited to three.

It is preferable that a constituent material from which the cutter 50 may be fabricated is strong enough to cut the plaque, calcified lesion or the like, and stainless steel, nitinol, Ta, Ti, Pt, Au, W, brass, a shape memory alloy, a supersteel alloy and the like can be suitably used, for example. In a case where a soft object such as a blood vessel is to be cut, a fluorine-based polymer such as polytetrafluoroethylene (PTFE) and a tetrafluoroethylene-ethylene copolymer (ETFE), polyetheretherketone (PEEK), polyimide, polyolefin such as polyethylene and polypropylene, polyamide, polyester such as polyethylene terephthalate and the like can be suitably used.

The protection tube 60 is a flexible tubular body disposed in the drive shaft 20 and the cutter 50. The protection tube 60 is not fixed to the drive shaft 20 and the cutter 50, and is disposed so as not to rotate together with the drive shaft 20. A guide wire lumen 61 into which a guide wire is inserted is formed in the protection tube 60. The protection tube 60 prevents the guide wire that passes through the inside of the drive shaft 20 from coming into direct contact with and rubbing against the drive shaft 20. A tubular protection tube stopper 62 is coupled to a distal end of the protection tube 60. A proximal end of the protection tube stopper 62 has an outer diameter larger than that of the protection tube 60 and covers the distal end of the protection tube 60. A distal end of the protection tube stopper 62 has an outer diameter smaller than that of the proximal end of the protection tube stopper 62 and protrudes toward the distal end side from the protection tube 60. The proximal end of the protection tube stopper 62 is disposed in a gap between the shaft portion 30 and the cutter 50 in an axial direction. Therefore, the protection tube stopper 62 can restrict movement of the protection tube 60 in the axial direction, and prevent the protection tube 60 from falling.

As illustrated in FIGS. 2 to 4, the bearing 80 includes a first bearing 81 and a second bearing 82 each having a ring shape. The first bearing 81 and the second bearing 82 are arranged so as to be spaced apart along the axis X (spaced apart from one another in the axial direction) inside a support tube 72. The first bearing 81 and the second bearing 82 have the same shape, but may have different shapes.

As illustrated in FIGS. 2 to 4, the shaft portion 30 is a site that rotatably supports the rotating structure 11 with respect to the housing unit 12. The shaft portion 30 is provided with a proximal end coupling portion 31 coupled to the drive shaft 20 and a distal end coupling portion 32 coupled to the cutter 50. The shaft portion 30 is further provided with a first sliding portion 33 supported by the first bearing 81, a second sliding portion 34 supported by the second bearing 82, and an intermediate shaft portion 35 disposed between the first sliding portion 33 and the second sliding portion 34. In the shaft portion 30, at least one (three, in the present embodiment) passage 40 extending along the axis X (extending along the axial direction) is formed.

The proximal end coupling portion 31 is disposed on a proximal end of the shaft portion 30 to which the distal end of the drive shaft 20 can be fitted and fixed by, for example, laser welding. The distal end coupling portion 32 is disposed on the distal end of the shaft portion 30 to which the cutter 50 can be fitted and fixed.

The first sliding portion 33 is a site disposed on the proximal end side of the distal end coupling portion 32 and rotatably supported by the first bearing 81. In the first sliding portion 33, three groove-shaped passages 40 extending in the axial direction are formed on an outer peripheral surface of a circular tube having a uniform outer diameter. The first sliding portion 33 includes three first rotary contact portions 41 that come into contact with an inner peripheral surface of the first bearing 81 between the three groove-shaped passages 40 regularly arranged in the circumferential direction. An outer diameter of the first rotary contact portion 41 is smaller than an inner diameter of the first bearing 81 to some extent. Therefore, the first rotary contact portion 41 slidably comes into contact with the inner peripheral surface of the first bearing 81.

The second sliding portion 34 is a site disposed on the distal end side of the proximal end coupling portion 31 and rotatably supported by the second bearing 82. In the second sliding portion 34, three groove-shaped passages 40 extending in the axial direction are formed on an outer peripheral surface of a circular tube having a uniform outer diameter. The second sliding portion 34 includes three second rotary contact portions 42 that come into contact with an inner peripheral surface of the second bearing 82 between the three groove-shaped passages 40 regularly arranged in the circumferential direction. An outer diameter of the second rotary contact portion 42 is smaller than an inner diameter of the second bearing 82 to some extent. Therefore, the second rotary contact portion 42 slidably comes into contact with the inner peripheral surface of the second bearing 82.

The intermediate shaft portion 35 is disposed between (axially between) the first sliding portion 33 and the second sliding portion 34. In the intermediate shaft portion 35, three groove-shaped passages 40 extending along the axis X (axial direction) are formed on an outer peripheral surface of a circular tube having a uniform outer diameter. The intermediate shaft portion 35 includes three protrusions 43 that protrudes radially outward from the first sliding portion 33 and the second sliding portion 34 between the three groove-shaped passages 40 regularly arranged in the circumferential direction.

The passage 40 forms a flow path for taking in the object cut by the cutter 50. A distal end of each passage 40 communicates with a proximal end of the cutout 53. The passage 40 is formed from the distal end side from the bearing 80 to the proximal end side of the bearing 80. The groove-shaped passage 40 may partially penetrate to an inner peripheral surface of the shaft portion 30. The passage 40 is connected to an outer peripheral surface of the shaft portion 30 on the distal end side from the bearing 80. As a result, a space of the passage 40 communicates with a space outside the shaft portion 30 on the distal end side from the bearing 80. The passage 40 is further connected to the outer peripheral surface of the shaft portion 30 on the proximal end side from the bearing 80. As a result, the space of the passage 40 communicates with the space outside the shaft portion 30 on the proximal end side from the bearing 80. Therefore, the passage 40 can take in the cut object from the outside of the shaft portion 30 on the distal end side from the bearing 80. The passage 40 can discharge the object taken in on the distal end side from the bearing 80 to the outside of the shaft portion 30 on the proximal end side from the bearing 80. By providing the passage 40 in the shaft portion 30, an intake opening 111 for taking in a cut piece can be located near the cutter 50. Furthermore, by providing the passage 40 in the shaft portion 30, friction between the shaft portion 30 and the bearing 80 is decreased, and slidability can be improved.

As illustrated in FIGS. 1 to 3, the outer tubular shaft 70 is a tubular body that houses the drive shaft 20 and the protection tube 60. The outer tubular shaft 70 includes an outer tubular main body 71 and a support tube 72 fixed to the distal end side of the outer tubular main body 71. An intake lumen 110 is formed between the outer tubular shaft 70 and the drive shaft 20 for taking in a small object obtained by cutting the plaque, calcified lesion or the like. The outer tubular shaft 70 includes the intake opening 111 on a distal end thereof for taking in the cut object or liquid discharged from the drive shaft 20. The distal end of the outer tubular shaft 70 is disposed with a predetermined gap G from a proximal end of the cutter 50 toward the proximal end side. The gap G has a length exceeding 0 (zero) along the axis X (axial direction) when the rotating structure 11 is disposed on the most proximal end side with respect to the housing unit 12. Therefore, the distal end of the outer tubular shaft 70 is prevented from coming into contact with the cutter 50. The outer tubular shaft 70 includes a proximal end opening 112 that opens inside the handle 90 on a proximal end thereof.

The outer tubular main body 71 is a tubular body having flexibility. The outer tubular main body 71 extends from the handle 90 to the vicinity of the cutter 50. The outer tubular main body 71 includes a curved portion 78 in which an extending direction of the outer tubular main body 71 changes on a distal end thereof. The curved portion 78 includes a first curved portion 78*a* on the distal end side and a second curved portion 78*b* on the proximal end side curved in opposite directions, and has an S-shape. The curved portion 78 is not limited to a portion curved twice, and may be curved once or may be curved three or more times. A proximal end of the outer tubular main body 71 is fixed to the handle 90. The proximal end opening 112 is disposed on the proximal end of the outer tubular main body 71.

The support tube 72 is a circular tube made of metal fixed to the distal end of the outer tubular main body 71. The support tube 72 is provided with a support tubular main body 113 having a certain inner diameter and a stopper 114 disposed on the distal end side of the support tubular main body 113 and having an inner diameter smaller than that of the support tubular main body 113. The intake opening 111 is disposed on a distal end of the support tube 72. The stopper 114 comes into contact with a distal end surface of the first bearing 81 of the bearing 80 described later. As a result, the stopper 114 restricts the first bearing 81 from moving toward the distal end side with respect to the support tube 72 and falling from the support tube 72. The stopper 114 can restrict the movement of the first bearing 81 as long as this (the stopper 114) can come into contact with the distal end surface of the first bearing 81, so that this (the stopper 114) may be separated from the first bearing 81 to some extent. The inner diameter of the stopper 114 is preferably smaller than an outer diameter of the first bearing 81 and larger than the inner diameter of the first bearing 81. A structure of the stopper 114 is not especially limited as long as this can restrict the movement of the first bearing 81, and for example, the stopper may be partially disposed in the circumferential direction.

As illustrated in FIG. 5, the outer tubular main body 71 includes a distal end tube 73 made of metal and a proximal end tube 75 disposed on the proximal end side from the distal end tube 73. The curved portion 78 of the outer tubular shaft 70 is formed in a range of the distal end tube 73. The proximal end tube 75 includes an inner tube 75*a* made of resin including a braided body formed of a thin metal wire therein, and an outer tube 75*b* made of metal that covers an outer surface of the inner tube 75*a*.

The distal end tube 73 includes a stepped portion 73*d* on a proximal end thereof. A distal end of the inner tube 75*a* of the proximal end tube 75 abuts the stepped portion 73*d* of the distal end tube 73. A proximal end surface of the distal end tube 73 and a distal end surface of the outer tube 75*b* are butted to each other, and the proximal end of the distal end tube 73 and an outer surface of a distal end of the outer tube 75*b* are coupled by a coupling member 77 made of metal.

On an outer surface of the distal end tube 73, a region from a proximal end of the support tube 72 to a distal end of the coupling member 77 is covered with a covering material 74 made of resin. An outer surface of the outer tube 75*b* forming the proximal end tube 75 is covered with a proximal end side covering material 76. A distal end position of the proximal end side covering material 76 is located on the proximal end side from a proximal end of the coupling member 77.

Figure 6:
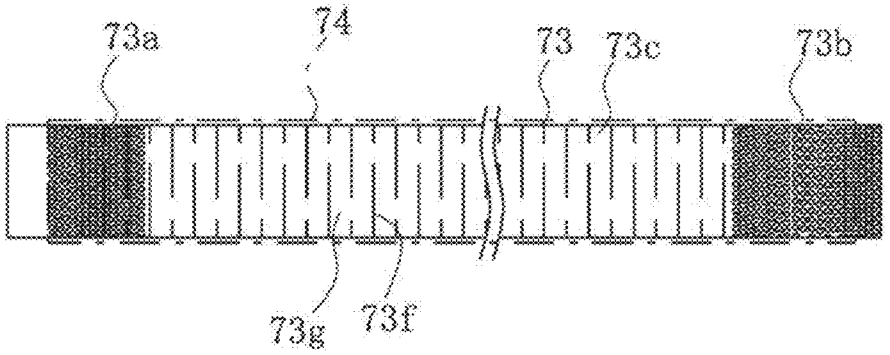
FIG. 6 is a front view of a distal end tube.

As illustrated in FIG. 6, the distal end tube 73 includes a distal end side rough surface portion 73*a* provided on an outer surface of a distal end and having an uneven shape, and a proximal end side rough surface portion 73*b* provided on an outer surface of a proximal end and having an uneven shape. In the distal end tube 73, an intermediate portion 73*c* is located between the distal end side rough surface portion 73*a* and the proximal end side rough surface portion 73*b*. The intermediate portion 73*c* includes a large number of slits 73*f* in the circumferential direction in order to increase flexibility, and includes smooth portions 73*g* including a smooth outer surface between the slits 73*f*. The distal end side rough surface portion 73*a* and the proximal end side rough surface portion 73*b* can be formed by applying roughening processing on the outer surface of the distal end tube 73. The roughening processing can be performed, for example, by irradiating the surface while shifting a focal point in a state in which an irradiation energy of a laser welding machine is weakened. The roughening processing may be a processing with sandpaper or dimpling processing.

In FIG. 5, in a long axis direction of the distal end tube 73 (axial direction of the distal end tube 73), the distal end side rough surface portion 73*a* is formed in a range of a region A, the proximal end side rough surface portion 73*b* is formed in a range of a region B, and the intermediate portion 73*c* is formed in a range of a region C. The covering material 74 is in close contact with the distal end tube 73 by entering the uneven shape of the distal end side rough surface portion 73*a* and the proximal end side rough surface portion 73*b*, and the covering material 74 does not enter the slit 73*f* of the intermediate portion 73*c* and is fixed to the distal end tube 73 only on the outer surface of the smooth portion 73*g*.

The distal end side rough surface portion 73*a*, a distal end position of which is located on the proximal end side from the distal end of the distal end tube 73, is not necessarily formed on the most distal end of the distal end tube 73 covered with the support tube 72. The proximal end side rough surface portion 73*b*, a proximal end position of which is at the same position as that of the proximal end of the distal end tube 73, is in contact with an inner surface of the coupling member 77. The coupling member 77 is joined to the distal end tube 73 with an adhesive; since the proximal end side rough surface portion 73*b* is formed up to the position of the coupling member 77, adhesion can be enhanced.

Figure 7:
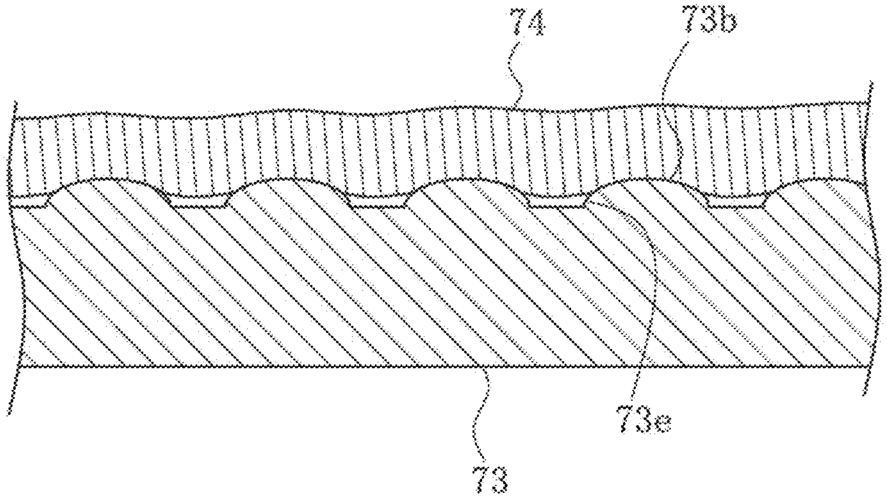
FIG. 7 is a cross-sectional view in a state in which a proximal end side rough surface portion of the distal end tube and a covering material are in close contact with each other.
Figure 8:
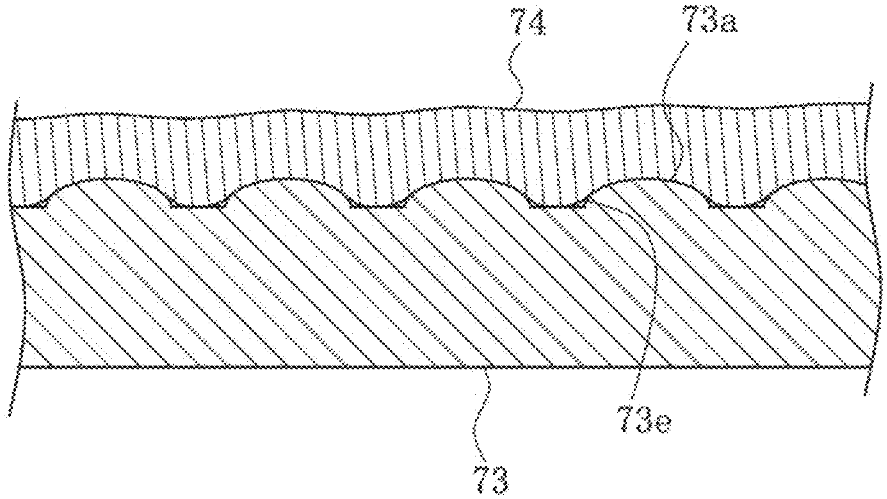
FIG. 8 is a cross-sectional view in a state in which a distal end side rough surface portion of the distal end tube and the covering material are in close contact with each other.
Figure 9:
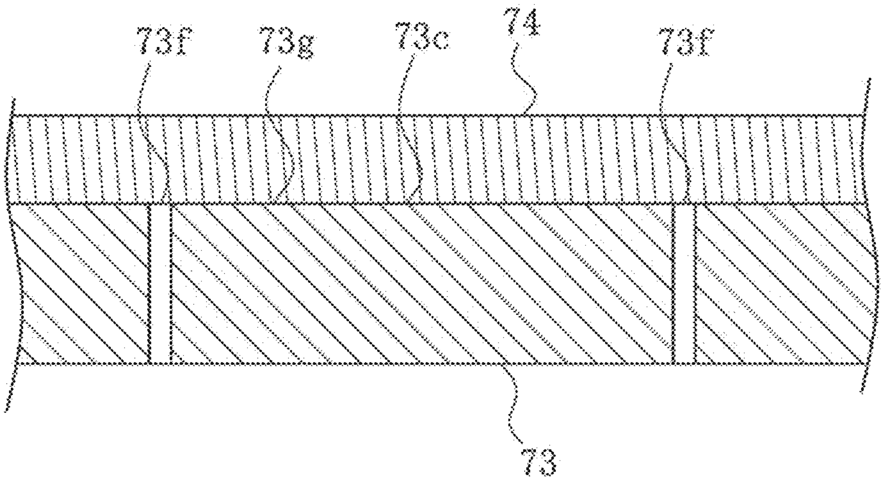
FIG. 9 is a cross-sectional view of a state in which the covering material is fixed to an intermediate portion of the distal end tube.

When the covering material 74 is fixed to the distal end tube 73, first, the distal end tube 73 is covered with a tubular covering material 74 and heated at first temperature (for example, about 210° C.) to shrink the covering material 74. At that time, the covering material 74 enters (is positioned in) the uneven shape of the distal end side rough surface portion 73*a* and the proximal end side rough surface portion 73*b* having the uneven shape and comes into close contact. As illustrated in FIG. 7, in the proximal end side rough surface portion 73*b* heated at the first temperature, an inner surface of the covering material 74 can be allowed to enter a concave portion (concavities) 73*e* of the uneven shape of the proximal end side rough surface portion 73*b*. Furthermore, by heating a portion of the distal end side rough surface portion 73*a* at second temperature (for example, about 230° C.) higher than the first temperature, a surface portion of the covering material 74 is melted, and the covering material 74 can be melted into the uneven shape of the distal end side rough surface portion 73*a* and further enters (is positioned in) the uneven shape of the distal end side rough surface portion 73. The first temperature and the second temperature can be optionally set according to a material of the covering material 74 or the like. As a result, as illustrated in FIG. 8, the inner surface of the covering material 74 can be allowed to enter more deeply the concave portion 73*e* of the uneven shape of the distal end side rough surface portion 73*a*. Both the distal end side rough surface portion 73*a* and the proximal end side rough surface portion 73*b* may be heated at the second temperature, and in this case, also in the proximal end side rough surface portion 73*b*, the inner surface of the covering material 74 can be allowed to enter the concave portion 73*e* more deeply as illustrated in FIG. 8. Therefore, the adhesion between the covering material 74 and the distal end tube 73 can be increased in the distal end side rough surface portion 73*a* and the proximal end side rough surface portion 73*b*, and the adhesion between the covering material 74 and the distal end tube 73 can be further increased in the distal end side rough surface portion 73*a* heated at the second temperature. As illustrated in FIG. 9, in the intermediate portion 73*c*, the covering material 74 does not enter the slit 73*f*, and the smooth portion 73*g* of the intermediate portion 73*c* and the inner surface of the covering material 74, which are smooth, are fixed adjacent to each other. Since the covering material 74 and the distal end tube 73 are in close contact with each other on the distal end and the proximal end, it is possible to prevent the covering material 74 from falling even when the covering material 74 receives external force such as when the covering material 74 comes into sliding contact with a blood vessel wall. In contrast, since the covering material 74 does not enter the slit 73*f* of the intermediate portion 73*c* of the distal end tube 73 and is fixed only by the smooth portion 73*g* of the intermediate portion 73*c*, the adhesion of the intermediate portion 73*c* with the covering material 74 does not increase and a decrease in flexibility can be prevented. In this manner, the covering material 74 enters (is positioned in) the distal end side rough surface portion 73*a* and the proximal end side rough surface portion 73*b* on the outer surface of the distal end tube 73 to be in close contact with the distal end tube 73, and the covering material 74 is fixed only to the outer surface of the smooth portion 73*g* of the intermediate portion 73*c*, so that the covering material 74 is brought into close contact with the distal end and the proximal end of the distal end tube 73, and it is possible to prevent a decrease in flexibility of the other regions, and it is possible to decrease friction between the distal end tube 73 and the blood vessel wall while securing flexibility in the distal end of the outer tubular shaft 70.

The distal end side rough surface portion 73*a* and the proximal end side rough surface portion 73*b* of the distal end tube 73 are desirably disposed in a portion other than the first curved portion 78*a* and the second curved portion 78*b* in the long axis (axial) direction. For example, the distal end side rough surface portion 73*a* can be disposed on the distal end side from the first curved portion 78*a*, and the proximal end side rough surface portion 73*b* can be disposed on the proximal end side from the second curved portion 78*b*. One of the distal end side rough surface portion 73*a* and the proximal end side rough surface portion 73*b* can be disposed between the first curved portion 78*a* and the second curved portion 78*b*.

The distal end tube 73 and the outer tube 75*b* of the proximal end tube 75 are formed of metal as described above. It is preferable that a constituent material thereof is strong to some extent, and stainless steel, nitinol, Ta, Ti, Pt, Au, W, a shape memory alloy and the like can be suitably used, for example.

The covering material 74 is formed of a flexible resin having excellent slidability. The covering material 74 is desirably melted at certain temperature. In the present embodiment, polyolefin is used as the covering material 74. The covering material 74 may be formed of another resin having the above-described property, and for example, a thermoplastic resin such as polyamide or polyurethane can be appropriately combined with a hydrophilic coating or the like.

The proximal end side covering material 76 can be formed of a resin harder than the covering material 74 that covers the distal end tube 73. As such resin, for example, a nylon elastomer, for example, Pebax (registered trademark) can be used. As a result, rigidity of the outer tubular shaft 70 can be increased, and operability including torque transmission performance can be made excellent. However, the material of the proximal end side covering material 76 may be another resin, and for example, PTFE, PET and the like can be used.

It is preferable that a constituent material from which the support tube 72 is fabricated is strong to some extent, and for example, stainless steel, nitinol, Ta, Ti, Pt, Au, W, a shape memory alloy, an engineering plastic such as polyether ether ketone (PEEK), and a combination thereof can be suitably used.

As illustrated in FIG. 5, an outer surface of the distal end of the drive shaft 20 is covered with a distal end covering portion 25 made of resin. The distal end covering portion 25 continuously extends from a proximal end surface of the shaft portion 30 toward the proximal end side from a coupling portion between the distal end tube 73 and the proximal end tube 75 in the long axis direction (axial direction). The distal end covering portion 25 extends so as to include a range of the curved portion 78 of the outer tubular shaft 70 in the long axis direction (axial direction). Since the outer tubular shaft 70 includes the S-shaped curved portion 78, the drive shaft 20 easily comes into contact with the first curved portion 78*a* and the second curved portion 78*b*, and at that time, the distal end covering portion 25 comes into contact with an inner surface of the outer tubular shaft 70, so that friction between them can be decreased. The inner tube 75*a* of the proximal end tube 75 includes a braided body made of metal therein as described above, and there is a case where the braided body is exposed inside on the distal end; however, since the distal end covering portion 25 is also provided at a joint between the distal end tube 72 and the proximal end tube 75, it is possible that the exposed braided body does not come into direct contact with a metal portion of the drive shaft 20, and durability of the drive shaft 20 can be improved.

As illustrated in FIG. 1, the handle 90 is provided with a casing 91, a drive unit 92, an intake port 93, a rotation operation portion 94, and a liquid delivery port 96.

A proximal end of the outer tubular main body 71 is fixed to a distal end of the casing 91. In the casing 91, an intake space 95 communicating with the intake port 93 and a liquid delivery space 97 communicating with the liquid delivery port 96 are formed. The proximal end opening 112 of the outer tubular main body 71 is rotatably disposed in the intake space 95.

The rotation operation portion 94 is a site operated by an operator with his/her finger to apply rotational torque to the outer tubular shaft 70. The rotation operation portion 94 is rotatably coupled to the distal end of the casing 91. The rotation operation portion 94 is fixed to an outer peripheral surface of the proximal end of the outer tubular main body 71.

The drive unit 92 is, for example, a hollow motor. The drive unit 92 is rotated by a battery not illustrated or externally supplied power. The drive shaft 20 is fixed to a hollow drive rotor of the hollow motor. A rotation speed of the drive unit 92 is not especially limited, and is 5,000 to 200,000 rpm, for example. The configuration of the drive unit 92 is not especially limited.

The intake port 93 conveys an object, liquid or the like in the intake space 95 to the outside. An intake drive source such as a pump or a syringe can be connected to the intake port 93. From the liquid delivery port 96, fluid can be delivered to the inside of the outer tubular shaft 70 via the liquid delivery space 97.

Next, a method of using the medical device 10 according to the present embodiment will be described using, as an example, a case where the lesion such as the plaque and calcified lesion in the blood vessel is cut and taken in.

Figure 10:
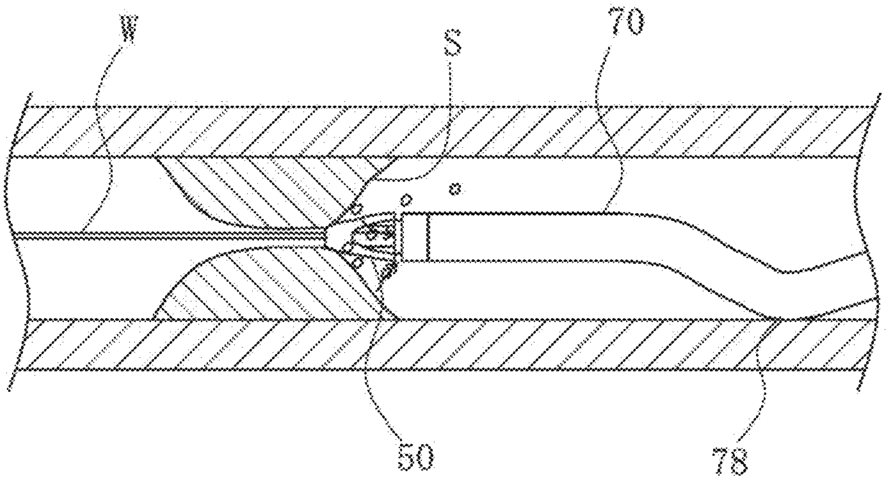
FIG. 10 is a schematic diagram illustrating a state in which cutting is performed by the medical device.

First, the operator inserts a guide wire W into the blood vessel and allows the same to reach the vicinity of a lesion S. Next, the operator inserts a proximal end of the guide wire W into the guide wire lumen 61 of the medical device 10. Thereafter, as illustrated in FIG. 10, the cutter 50 is moved to the vicinity of the lesion S using the guide wire W as a guide. At that time, since the distal end tube 72 forming the distal end of the outer tubular shaft 70 is provided with the covering material 76 made of resin, friction with the blood vessel wall can be controlled to be low. Therefore, it is possible to prevent torque from being accumulated in the outer tubular shaft 70 in a case where this is inserted into a path of the blood vessel bent a plurality of times.

Next, the operator operates the drive unit 92. As a result, the drive shaft 20 rotates, and the cutter 50 and the shaft portion 30 rotate together with the drive shaft 20. As a result, the operator can cut the lesion S by the cutter 50. At that time, especially in the curved portion 78, the inner surface of the outer tubular shaft 70 and the drive shaft 20 rotating at a high speed might come into contact with each other, but since the distal end covering portion 25 made of resin is provided on the distal end of the drive shaft 20, friction between the drive shaft 20 and the outer tubular shaft 70 can be controlled to be low.

The operator can reciprocate the outer tubular shaft 70 in a longitudinal direction of the blood vessel by moving the entire handle 90 or the outer tubular shaft 70 exposed to the outside of the body. As a result, the operator can cut the lesion S in the longitudinal direction of the blood vessel by the cutter 50.

The additional coil 23 can generate the flow of fluid that conveys an object toward the proximal end side in the intake lumen 110 as the drive shaft 20 rotates. Therefore, the lesion S cut by the cutter 50 becomes debris, and is taken in the intake lumen 110 from the distal end opening. The debris can pass through the cutout 53 of the cutter 50 and efficiently enter the passage 40 communicating with the cutout 53. The debris can enter the passage 40 from the gap G between the cutter 50 and the support tube 72. The passage 40 can be formed spirally around the axis X. As a result, when the drive shaft 20 rotates by the rotating passage 40, the spiral passage 40 that rotates can function as an Archimedean screw (screw pump). As a result, the passage 40 can smoothly convey the object or fluid inside the intake lumen 110 toward the proximal end side.

The debris that enters the passage 40 on the distal end side from the first bearing 81 moves toward the proximal end side inside the first bearing 81 and the second bearing 82. Thereafter, the debris moves from the passage 40 to the outer peripheral surface side of the shaft portion 30 on the proximal end side from the second bearing 82. Thereafter, the debris moves toward the proximal end side in the intake lumen 110 and is discharged through the intake space 95 and the intake port 93. After the cutting of the lesion S and the intake of the debris are completed, the operator stops the operation of the drive unit 92. As a result, the cutting of the lesion S and the discharge of the debris stop. Thereafter, the operator removes the medical device 10 from the blood vessel, and the treatment is completed.

As described above, (1) a medical device 10 according to the present embodiment is a medical device 10 including a long shaft 70, the shaft 70 including a distal end tube 73 made of metal, the distal end tube 73 provided with a distal end side rough surface portion 73*a* having an uneven shape provided on an outer surface of a distal end, a proximal end side rough surface portion 73*b* having an uneven shape provided on an outer surface of a proximal end, and an intermediate portion 73*c* as a region between the distal end side rough surface portion 73*a* and the proximal end side rough surface portion 73*b* including a smooth outer surface, the distal end tube 73 including an outer surface covered with a covering material 74 made of resin, and the covering material 74 being in close contact with the distal end side rough surface portion 73*a* and the proximal end side rough surface portion 73*b*. In the medical device 10 configured as described above, since the covering material 74 enters the uneven shape of the distal end tube 73 on the distal end side rough surface portion 73*a* and the proximal end side rough surface portion 73*b* and is closely fixed, it is possible to increase fixing strength of the covering material 74 with respect to the distal end tube 73 for decreasing friction with the blood vessel wall. In the medical device 10, since the outer surface of the intermediate portion 73*c* of the distal end tube 73 is smooth, the covering material 74 does not enter the uneven shape, and a decrease in flexibility can be prevented.

(2) In the medical device 10 according to (1) above, the shaft 70 may include a curved portion 78 shaped in a region of the distal end tube 73, and the curved portion 78 may be located in the intermediate portion 73*c*. Since the intermediate portion 73*c* has high flexibility without the covering material 74 entering the same, the medical device 10 can make the curved portion 78 flexible to improve passability of the shaft 70 in the blood vessel.

(3) In the medical device 10 according to (1) or (2) above, the distal end side rough surface portion 73*a* may include a distal end position on a distal end of the covering material 74, and the proximal end side rough surface portion 73*b* may include a proximal end position on a proximal end side from a proximal end of the covering material 74. As a result, the medical device 10 can increase the adhesion between a member provided on the proximal end side from the covering material 74 and the distal end tube 73 and increase joining strength of the distal end tube 73.

(4) In the medical device 10 according to any one of (1) to (3) above, in at least one of the distal end side rough surface portion 73*a* and the proximal end side rough surface portion 73*b*, the covering material 74 may enter a concave portion 73*e* of an uneven shape. As a result, in the medical device 10, the adhesion between the distal end tube 73 and the covering material 74 is improved, and the covering material 74 can be prevented from falling from the distal end tube 73.

(5) In the medical device 10 according to any one of (1) to (4) above, the intermediate portion 73*c* may include a slit 73*f* and a smooth portion 73*g* including a smooth outer surface, and the smooth portion 73*g* and the covering material 74 may be fixed. Since the covering material 74 is fixed to the smooth portion 73*g* and does not enter the inside of the slit 73*f*, it is possible to increase the fixing strength of the covering material 74 while suppressing a decrease in flexibility of the distal end tube 73.

(6) In the medical device 10 according to any one of (1) to (3) above, in the distal end side rough surface portion 73*a* and the proximal end side rough surface portion 73*b*, the covering material 74 may enter a concave portion 73*e* of the uneven shape, and in the distal end side rough surface portion 73*a*, the covering material 74 may enter the concave portion 73*e* more deeply than the proximal end side rough surface portion 73*b*. As a result, it is possible to further increase the degree of adhesion of the covering material 74 on the distal end side of the distal end tube 73 and increase the fixing strength.

(7) In the medical device 10 according to any one of (1) to (6) above, the shaft 70 may include a proximal end tube 75 made of metal on a proximal end side of the distal end tube 73, an outer surface of the proximal end tube 75 may be covered with a proximal end side covering material 76 made of resin, and the covering material 74 may be more flexible than the proximal end side covering material 76. As a result, the medical device 10 can increase the flexibility of the distal end of the shaft 70 while securing rigidity of the proximal end of the shaft 70 and increasing the torque transmission performance and push-in performance.

The new medical device disclosed here is not limited to the embodiment described above, and various modifications can be made by those skilled in the art within the technical idea of the present invention. The medical device 10 is not limited to the device that cuts and removes the object in the blood vessel, and the present invention can also be applied to other types of devices including the tube made of metal on the distal end such as an ultrasonic catheter, for example.

The detailed description above describes embodiments of a medical device, operational method and method of manufacture representing examples of the new medical device, operation and manufacturing method disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents that fall within the scope of the claims are embraced by the claims.

What is claimed is:

1. A medical device comprising:
an elongated shaft;
the shaft including a distal end tube made of metal;
the distal end tube including a distal end and a proximal end, the distal end tube being provided with: i) a distal end side rough surface portion having an uneven shape provided on an outer surface of the distal end; ii) a proximal end side rough surface portion having an uneven shape provided on an outer surface of the proximal end; and iii) an intermediate portion as a region between the distal end side rough surface portion and the proximal end side rough surface portion including a smooth outer surface;
the distal end tube including an outer surface covered with a covering material made of resin; and
the covering material being in close contact with the distal end side rough surface portion and the proximal end side rough surface portion.

2. The medical device according to claim 1, wherein the shaft includes a curved portion in the intermediate portion of the distal end tube.

3. The medical device according to claim 1, wherein
at least a part of the distal end side rough surface portion is covered by the covering material, and
the proximal end side rough surface portion includes a proximal end position on a proximal end side from a proximal end of the covering material.

4. The medical device according to claim 1, wherein the uneven shape of the distal end side rough surface portion includes a concave portion and the uneven shape of the proximal end side rough surface portion includes a concave portion, and the covering material in at least one of the distal end side rough surface portion and the proximal end side rough surface portion is positioned at least partly in the concave portion of the uneven shape.

5. The medical device according to claim 4, wherein the intermediate portion includes a slit and a smooth portion including a smooth outer surface, the covering material being fixed to the smooth portion of the intermediate portion.

6. The medical device according to claim 1, wherein the uneven shape of the distal end side rough surface portion includes a concave portion and the uneven shape of the proximal end side rough surface portion includes a concave portion, and the covering material,
in the distal end side rough surface portion and the proximal end side rough surface portion, the covering material is at least partially positioned in the uneven shape, and
in the distal end side rough surface portion, the covering material is positioned in the concave portion more deeply than in the proximal end side rough surface portion.

7. The medical device according to claim 1, wherein
the shaft includes a proximal end tube made of metal on a proximal end side of the distal end tube,
an outer surface of the proximal end tube is covered with a proximal end side covering material made of resin, and
the covering material covering the outer surface of the distal end tube is more flexible than the proximal end side covering material.

8. A medical device positionable in a biological lumen, the medical device comprising:
a rotatable shaft;
a cutter configured to cut an object located in the biological lumen, the cutter being connected to the shaft so that rotation of the shaft results in rotation of the cutter;
an outer tubular main body in which the rotatable shaft is positioned, the outer tubular main body having a distal end, the cutter being positioned distal of the distal end of the outer tubular main body;

the outer tubular main body including a distal end metal tube constituting a distal portion of the outer tubular main body, the distal end metal tube having an outer surface;

the distal end metal tube including a first rough surface portion having an uneven outer surface and a second rough surface portion having an uneven outer surface, the first rough surface portion being located distal of the second rough surface portion;

the uneven outer surface of the first rough surface portion extending from a distal end of the first rough surface portion to a proximal end of the first rough surface portion;

the uneven outer surface of the second rough surface portion extending from a distal end of the second rough surface portion to a proximal end of the second rough surface portion;

the proximal end of the first rough surface portion being spaced apart from the distal end of the second rough surface portion, with an intermediate portion of the distal end metal tube being located between the proximal end of the first rough surface portion and the distal end of the second rough surface portion;

the intermediate portion of the distal end metal tube having an outer surface configured differently from the uneven outer surface of the first rough surface portion and the uneven outer surface of the second rough surface portion; and the distal end metal tube including a covering material made of resin, the covering material made of resin covering: i) the uneven outer surface of the first rough surface portion of the distal end metal tube; ii) the intermediate portion of the distal end metal tube; and iii) the uneven outer surface of the second rough surface portion of the distal end metal tube.

9. The medical device according to claim 8, wherein the intermediate portion of the distal end metal tube includes a plurality of spaced apart slits that pass through the distal end metal tube and smooth surface portions between the plurality of slits.

10. The medical device according to claim 9, wherein the covering material is fixed to the smooth surface portions of the intermediate portion of the distal end metal tube, the covering material covering the intermediate portion of the distal end metal tube not being positioned in the plurality of slits.

11. The medical device according to claim 8, wherein the covering material is adhered to portions of the intermediate portion of the distal end metal tube and not being adhered to other portions of the intermediate portion of the distal end metal tube.

12. The medical device according to claim 8, wherein the distal end metal tube includes a distal end and a proximal end, the uneven outer surface of the first rough surface portion terminating at a distal end of the uneven outer surface of the first rough surface portion that is spaced proximally from the distal end of the distal end metal tube, and the uneven outer surface of the second rough surface portion terminating at a proximal end of the uneven outer surface of the second rough surface portion that is coincident with the proximal end of the distal end metal tube.

13. The medical device according to claim 8, wherein the uneven outer surface of the second rough surface portion terminates at a proximal end of the uneven outer surface of the second rough surface portion, the proximal end of the uneven outer surface of the second rough surface portion extending proximally beyond a proximal end of the covering material.

14. The medical device according to claim 8, wherein the outer tubular main body includes a proximal end tube constituting a proximal portion of the outer tubular main body, the proximal end tube being positioned proximal of the distal end metal tube, and including a covering material that covers the proximal end tube.

15. The medical device according to claim 14, wherein the covering material covering the proximal end tube is made of a resin that is harder than the resin from which the covering material that coves the distal end metal tube is made.

16. The medical device according to claim 8, wherein the covering material has an outer surface that is an outermost surface of the outer tubular main body.

17. The medical device according to claim 8, wherein the uneven outer surface of the first rough surface portion includes a plurality of concavities and the uneven outer surface of the second rough surface portion includes a plurality of concavities, the covering material being at least partially positioned in the concavities of the uneven outer surface of the first rough surface portion, the covering material being at least partially positioned in the concavities of the uneven outer surface of the second rough surface portion.

18. The medical device according to claim 17, wherein the covering material is positioned more deeply in the concavities of the uneven outer surface of the second rough surface portion than the concavities of the uneven outer surface of the first rough surface portion.

19. A method for producing a distal end tube forming part of a medical device that is positionable in a biological lumen, the method comprising:

performing roughening processing on first and second portions of an outer surface of a metal tube that is configured to be positioned in the biological lumen;

the performing of the roughening processing including: i) performing the roughening processing on the first portion of the outer surface of the metal tube to produce a first rough surface portion having an uneven outer surface; and ii) performing the roughening processing on the second portion of the outer surface of the metal tube to produce a second rough surface portion having an uneven outer surface;

the performing of the roughening processing being carried out so that: i) the first rough surface portion is located distal of the second rough surface portion; ii) the uneven outer surface of the first rough surface portion extends from a distal end of the first rough surface portion to a proximal end of the first rough surface portion; iii) the uneven outer surface of the second rough surface portion extends from a distal end of the second rough surface portion to a proximal end of the second rough surface portion; and i) the proximal end of the first rough surface portion is spaced apart from the distal end of the second rough surface portion;

the performing of the roughening processing on the outer surface of the first portion of the metal tube and the performing of the roughening processing on the outer surface of the second portion of the metal tube being carried out so that the outer surface of an intermediate portion of the metal tube is a smooth outer surface, the intermediate portion of the metal tube having the smooth outer surface being located between the proximal end of the first rough surface portion and the distal end of the second rough surface portion;

fixing a covering material made of resin to the metal tube so that the covering material covers the uneven outer surface of the first rough surface portion of the metal tube, the uneven outer surface of the second rough surface portion of the metal tube and the smooth outer surface of the intermediate portion of the metal tube; and the covering material being in contact with the uneven outer surface of the first rough surface portion and the uneven outer surface of the second rough surface portion.

20. The method according to claim 19, wherein the uneven outer surface of the first rough surface portion and the uneven outer surface of the second rough surface portion include concavities, the intermediate portion of the metal tube having the smooth outer surface including a plurality of spaced apart slits that pass through the metal tube, the fixing of the covering material made of resin to the metal tube including covering the metal tube with a tubular covering material and heating the tubular covering material to shrink the covering material onto the metal tube, the method further comprising heating the first rough surface portion of the metal tube and the second rough surface portion of the metal tube so that the covering material made of resin at least partially enters the concavities of the uneven outer surface of the first rough surface portion and the concavities of the uneven outer surface of the second rough surface.

* * * * *